United States Patent [19]

Brendel et al.

[11] Patent Number: 5,360,812
[45] Date of Patent: Nov. 1, 1994

[54] FUSED 1,2,5-OXADIAZOLE-2-OXIDES AND THEIR USE

[75] Inventors: Joachim Brendel, Frankfurt am Main; Karl Schönafinger, Alzenau; Helmut Bohn, Schöneck, all of Germany

[73] Assignee: Cassella Aktiengesellschaft, Frankfurt am Main, Germany

[21] Appl. No.: 67,520

[22] Filed: May 25, 1993

[30] Foreign Application Priority Data

Jun. 10, 1992 [DE] Germany .................. 4218977

[51] Int. Cl.$^5$ .................. C07D 495/04; A61K 31/41
[52] U.S. Cl. .................. 514/364; 548/126; 546/116
[58] Field of Search .................. 548/126; 514/364

[56] References Cited

U.S. PATENT DOCUMENTS 4,416,893 11/1983 Schonafinger ............ 548/125

FOREIGN PATENT DOCUMENTS 0431944 6/1991 European Pat. Off. .
2017690 10/1979 United Kingdom .

OTHER PUBLICATIONS

Paulmier et al., CA 84:43919h 1976.
Paulmier et al., CA 84:43941j 1976.
Von Dobeneck et al., CA 90:87350u 1979.
Noto et al., CA 111:56750x 1989.
J. Chem. Soc., Perkin Trans. 2, No. 2 (1989) pp. 127–130.

Chem. Abs., vol. 113, No. 3, (1990), Abs. No. 23596q.

*Primary Examiner*—Jane T. Fan
*Attorney, Agent, or Firm*—Perman & Green

[57] ABSTRACT

The present invention relates to fused 1,2,5-oxadiazole-2-oxides of the general formula I

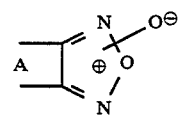

in which
A denotes

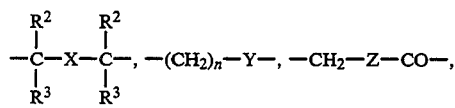

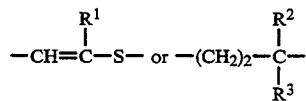

and X, Y, Z as well as $R^1$, $R^2$, $R^3$ and n are defined as indicated in Claim 1, to processes for their preparation and to their use for the control and prevention of disorders of the cardiovascular system, in particular for the control and prevention of angina pectoris, and for the treatment of erectile dysfunctions.

6 Claims, No Drawings

FUSED 1,2,5-OXADIAZOLE-2-OXIDES AND THEIR USE

BACKGROUND OF THE INVENTION

1. Field of the Invention

The present invention relates to fused 1,2,5-oxadiazole-2-oxides, their preparation and their use as pharmacological active compounds.

2. Discussion of the Prior Art

A number of fused, 1,2,5-oxadiazole-2-oxides are already known and described, for example, in DE-A-2,912,447.

SUMMARY OF THE INVENTION

The present invention relates to fused 1,2,5-oxadiazole-2-oxides of the general formula I

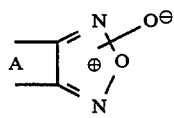

in which

A denotes

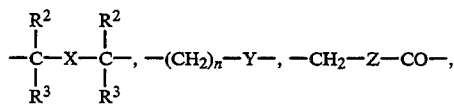

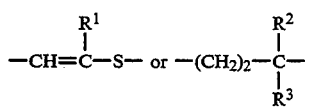

n represents 2 or 3;

X denotes —O—, —N(R$^2$)—, —N(COR$^4$)—, —S—, —S(O)—, —S(O)$_2$—, —CH$_2$— or —CH$_2$CH$_2$—;

Y denotes —S—, —S(O)—, —S(O)$_2$—,

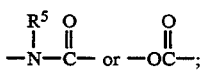

Z denotes —C(R$^2$R$^3$)—, —O—, —S—, —N(H)—, —N(CH$_3$)—,

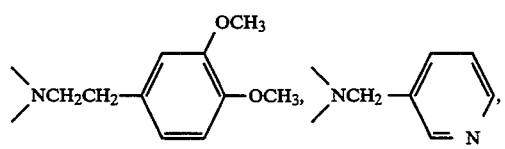

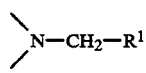

or —CH$_2$—;

R$^1$ denotes —COOH, —COOR$^6$ or —CONR$^2$R$^3$;
R$^2$ denotes hydrogen or (C$_1$–C$_6$)-alkyl;
R$^3$ denotes (C$_1$–C$_6$)-alkyl;
R$^4$ denotes hydrogen, (C$_1$–C$_6$)-alkyl, or optionally substituted aryl;
R$^5$ denotes hydrogen, (C$_1$–C$_6$)-alkyl, (C$_2$–C$_4$)-alkenyl, optionally substituted aryl, —(CH$_2$)$_p$—R$^7$, —CH$_2$COOR$^2$, —CH$_2$CONR$^2$R$^3$, —CH$_2$CON B or —(CH$_2$)$_r$D;

R$^6$ denotes (C$_2$–C$_4$)-alkyl;
R$^7$ denotes optionally substituted aryl or heteroaryl;
B denotes —(CH$_2$)$_q$—, —(CH$_2$)$_2$—O—(CH$_2$)$_2$— or

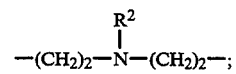

D denotes —OH, —OR$^2$ or —NR$^2$R$^3$; and
p represents 1, 2 or 3;
q represents 4, 5 or 6; and
r represents 2, 3 or 4, and their pharmacologically acceptable acid addition compounds.

Alkyl radicals representing R$^2$, R$^3$, R$^4$, R$^5$ or R$^6$ can be straight-chain or branched. Examples of alkyl radicals of this type are methyl, ethyl, n-propyl, i-propyl, n-butyl, i-butyl, pentyl and hexyl.

(C$_2$–C$_4$)-alkenyl representing R$^5$ can also be straight-chain or branched. Examples are vinyl and allyl.

Aryl representing R$^4$, R$^5$ or R$^7$ is in particular (C$_6$–C$_{14}$)-aryl, phenyl being preferred.

Heteroaryl representing R$^7$ is preferably 5- to 7-membered and is derived, for example, from pyrrole or pyridine. α-Pyridyl and β-pyridyl are preferred.

Aryl and heteroaryl representing R$^4$, R$^5$ or R$^7$ can also be substituted. Suitable substituents are, for example, (C$_1$–C$_4$)-alkyl, (C$_1$–C$_4$)-alkoxy, amino, (C$_1$–C$_4$)-alkylamino, di-(C$_1$–C$_4$)-alkylamino, (C$_1$–C$_6$)-alkanoylamino, halogen, preferably fluorine, chlorine or bromine, hydroxyl, nitro or cyano. Aryl or heteroaryl can also be polysubstituted by the said substituents, for example disubstituted or trisubstituted.

A preferred substituted aryl radical is 3,4-dimethoxyphenyl.

The following are also preferred:
n 2
R$^2$ hydrogen, methyl
R$^3$ methyl, ethyl
R$^4$ methyl, phenyl
R$^6$ ethyl
R$^7$ phenyl, 3,4-dimethoxyphenyl, 2-pyridyl, 3-pyridyl
p 1, 2
q 4, 5
r 2, 3

The following are particularly preferred:
X —O—, —N(H)—, —N(CH$_3$)—, —N(COphenyl)—, —N(COCH$_3$)—, —CH$_2$—, —CH$_2$CH$_2$—
Y

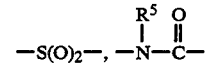

Z

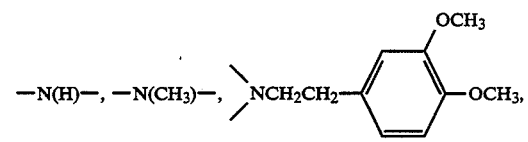

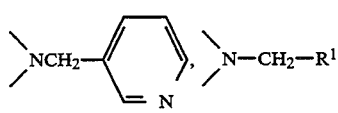

$R^1$ —COOH, —COOC$_2$H$_5$, —COONHCH$_3$
$R^5$ hydrogen, —CH$_3$, —C$_2$H$_5$, —phenyl, —(C$_2$-)$_p$—R$^7$, —CH$_2$COOR$^2$, —CH$_2$CONR$^2$R$^3$, —CH$_2$-CONB, —(CH$_2$)$_r$D The compounds of the general formula I according to the invention can be prepared by oxidising 1,2-dioximes of the general formula II

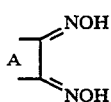

in which A is defined as indicated above.

Oxidising agents which can be employed for this reaction, which is known per se, are hypohalites such as sodium hypochlorite or potassium hypochlorite or sodium hypobromite or potassium hypobromite, metal salts such as potassium hexacyanoferrate(III) or lead tetraacetate, nitrous gases such as NO$_2$ or iodoso compounds such as, for example, bis(trifluoroacetoxy)iodobenzene.

Depending on the configuration of the oximes employed and the reaction conditions used, two isomers of the general formula I having a different position of the N-oxide function, i.e. 1-oxide or 3-oxide compounds, can result from dioximes of the general formula II having an unsymmetrical radical A.

Compounds of the general formula I where A=—(CH$_2$)$_n$Y— or —CH$_2$—Z—CO— can be rearranged to each other by heating to 80° to 140° C. in an inert solvent, such as, for example, toluene or petroleum ether. The individual isomers can be isolated as pure compounds from the equilibrium mixtures thus obtained by customary separation processes, such as, for example, crystallisation or chromatography.

For the applications of the compounds of the general formula I, however, the separation of the isomers is not absolutely necessary, so it can also be omitted.

In compounds of the general formula I where A=—CH=CR$^1$—S—, a separation of this type is not possible since these isomers rapidly rearrange to each other even at room temperature.

The present invention accordingly also relates to isomer mixtures of fused 1,2,5-oxadiazole-2-oxides of the general formula I, in which
A denotes —(CH$_2$)$_n$—Y—, —CH$_2$—Z—CO—, —CH=CR$^1$—S—, or —(CH$_2$)$_2$CR$^2$R$^3$— and Y, Z, R$^1$, R$^2$, R$^3$ and n are defined as indicated above.

The 1,2-dioximes of the general formula II can either be obtained from 1,2-diones of the general formula III

or from 1,2-dione monooximes of the general formula IV

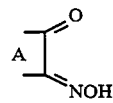

by reaction with excess hydroxylamine (see, for example, Houben-Weyl, Methoden der organischem Chemie (Methods of Organic Chemistry), Volume X/4, pages 55 to 77).

The compounds of the general formulae III and IV are either known or can be prepared by known methods.

For example, compounds of the general formula V

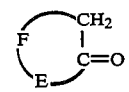

in which E denotes —C(R$^2$R$^3$)—,

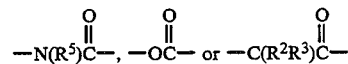

F is selected such that E and F together give A according to the above definitions and R$^2$, R$^3$ and R$^5$ are defined as indicated above, can be converted into dione monoximes of the general formula IV by nitrosation of the methylene group, for example with sodium nitrite in hydrochloric or acetic acid (see, for example, H. V. Dobeneck et al., Liebigs Ann. Chem. 1976, 476) or with amyl nitrite in the presence of an alkali metal alkoxide (see, for example, C. Sandris, G. Ourisson, Bull. Soc. Chim. Fr. 1958, 345, Houben-Weyl, Volume X/4, pages 17–44) or alternatively by oxidation, for example with selenium dioxide (see, for example, C. Sandris, G. Ourisson, Bull. Soc. Chim. Fr. 1958, 345, Houben-Weyl, Volume 4/1a, pages 351–353), into diones of the general formula III.

Alternatively, however, compounds of the general formula VI

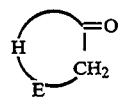

in which G denotes

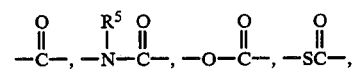

—S—, —S(O) or —S(O)$_2$ H is selected such that G and H together give A according to the above definitions and R$^5$ is defined as indicated above, can also be nitrosated by reaction with sodium nitrite in aqueous hydrochloric acid. By this means, compounds of the general formula IV are also obtained (see, for example, J. Ackrell, A. J. Boulton, J. Chem. Soc. Perkin Trans. I 1973, 351).

The preparation of compounds of the general formula VI is known and described, for example, in EP-A 149,534, J. Antibiotics 33 (1980), 173 and J. Chem. Soc. (C) 1967, 2171.

For the synthesis of compounds of the general formula I where A=—CH=C(R¹)—S—, it is preferred to convert a compound of the general formula VII

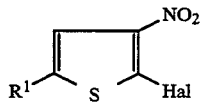

in which Hal denotes chlorine or bromine and R¹ is defined as indicated above, with sodium azide into compounds of the general formula Ia according to the invention

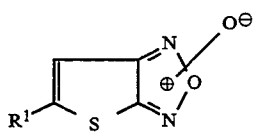

(see, for example, J. Chem. Soc. Perkin Trans II, 1989, 127).

In addition to the compounds described in the Examples, the following compounds according to the invention can also be prepared according to the above preparation processes:

5-phenyl-6,7-dihydro[1,2,5]oxadiazolo[3,4-c]pyridin-4(5H)-one-1-oxide and -3-oxide, and also the corresponding 5-(3-pyridylmethyl), 5-methyl, 5-ethyl, 5-propyl, 5-isopropyl, 5-butyl, 5-hexyl, 5-allyl, 5-(3,4-dimethoxybenzyl), 5-(3,4-dimethoxyphenylethyl), 5-(N,N-diethylaminoethyl), 5-(N,N-dimethylaminocarbonylmethyl) and 5-hydroxyethyl compounds;

6,7-dihydro[1,2,5]oxadiazolo[3,4-c]pyridin-4(5H)-one-1-oxide and -3-oxide;

5,6,7,8-tetrahydro[1,2,5]oxadiazolo[3,4-c]azepin-4-one-1-oxide and -3-oxide;

5-benzyl-5,6,7,8-tetrahydro[1,2,5]oxadiazolo[3,4-c]azepin-4-one-1-oxide and -3-oxide, and also the corresponding 5-(3-pyridylmethyl) compounds;

5,6-dihydrothieno[2,3-c][1,2,5]oxadiazole-1-oxide and -3-oxide and also the corresponding 4-oxo derivatives;

6,7-dihydro[1,2,5]oxadiazolo[3,4-c]pyran-4-one-1-oxide and -3-oxide;

5-methyl-5,6-dihydro-4,4,6,6-tetramethyl-4H-pyrrolo[3,4-c][1,2,5]oxadiazole-1-oxide and also the corresponding 5-acetyl compound;

4,5,6,7-tetrahydro-4,4,7,7-tetramethylbenzofurazan-1-oxide;

4,5,6,7-tetrahydro-4,7-dimethylbenzofurazan-1-oxide;

5,6-dihydro-cyclopent[c][1,2,5]oxadiazol-4(4H)-one-1-oxide and -3-oxide;

5,6-dihydro-5,5-dimethyl-cyclopent[c][1,2,5]oxadiazol-4(4H)-one-1-oxide and -3-oxide;

thieno[2,3-c][1,2,5]oxadiazole-5-carboxamide-1-oxide and -3-oxide and also the corresponding 5-N-ethyl-carboxamide compounds;

4-methyl- and 6-methyl-5,6-dihydro-4H-cyclopent[c][1,2,5]oxadiazole-1-oxide and also the corresponding 4,4-diethyl and 6,6-diethyl compounds;

4H, 6H-4,6-dimethylfuro[3,4-c][1,2,5]oxadiazole-1-oxide;

4H, 6H-furo[3,4-c][1,2,5]oxadiazol-4-one-1-oxide and -3-oxide and also the corresponding 4H, 6H-thieno compounds;

5,6-dihydro-5-(3-pyridylmethyl)-4H-pyrrolo[3,4-c][1,2,5]-oxadiazol-4-one-1-oxide and -3-oxide and also the corresponding 5-hydroxycarbonylmethyl compounds.

Compounds of the general formula I according to the invention which contain a basic group can form salts with inorganic or organic acids. Suitable acids for the formation of pharmacologically acceptable acid addition salts are, for example: hydrogen chloride, hydrogen bromide, naphthalenedisulphonic acids, in particular 1,5-naphthalenedisulphonic acid, phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, isonicotinic, methanesulphonic, p-toluenesulphonic, citric or adipic acid. The acid addition salts can be prepared in the customary manner by combination of the components, expediently in a suitable solvent or diluent.

The compounds of the general formula I and their pharmacologically acceptable acid addition salts have useful pharmacological properties. In the potassium-depolarised guinea-pig pulmonary artery model, they lead to a relaxation at low concentrations. This action can be inhibited with oxyhaemoglobin, which points to an NO-mediated mechanism. As an activator of guanylate cyclase, nitrogen monoxide leads to an increase in cyclic guanosine monophosphate, which causes a relaxation in the smooth muscle and antiadhesive and antiaggregatory actions in the blood platelets. In addition, nitrogen monoxide is also crucially involved in learning processes, in the regulation of kidney function, in immune defence, in septic shock and in erectile dysfunctions. The compounds of the general formula I, their pharmacologically acceptable acid addition salts and their isomer mixtures can thus be employed in the indications mentioned. Above all, however, NO donors have proven suitable for the treatment and prophylaxis of angina pectoris.

The compounds of the general formula I and their pharmacologically acceptable acid addition salts and isomer mixtures can therefore be administered to humans as medicines per se, in mixtures with one another or in the form of pharmaceutical preparations which permit enteral or parenteral use and which as active constituent contain an effective dose of at least one compound of the general formula I or of an acid addition salt thereof or of an isomer mixture, in addition to customary pharmaceutically innocuous excipients and additives.

The medicines can be administered orally, for example in the form of pills, tablets, coated tablets, sugar-coated tablets, hard and soft gelatin capsules, solutions, syrups, emulsions or suspensions, or aerosol mixtures. However, administration can also be carried out rectally, for example in the form of suppositories, or parenterally, for example in the form of injection solutions, or percutaneously, for example in the form of ointments or tinctures.

For the production of the pharmaceutical preparations, pharmaceutically inert inorganic or organic excipients can be used. For the preparation of pills, tablets, sugar-coated tablets and hard gelatin capsules, lactose, maize starch or derivatives thereof, talc, stearic acid or its salts, etc., for example can be used. Excipients for soft gelatin capsules and suppositories are, for example, fats, waxes, semi-solid and liquid polyols, natural or hardened oils, etc. Suitable excipients for the preparation of solutions and syrups are, for example, water, sucrose, invert sugar, glucose, polyols, etc. Suitable excipients for the preparation of injection solutions are, for example, water, alcohols, glycerol, polyols or vegetable oils.

In addition to the active compounds and excipients, the pharmaceutical preparations can also contain additives, such as, for example, fillers, extenders, disintegrants, binders, lubricants, wetting agents, stabilisers, emulsifiers, preservatives, sweeteners, colorants, flavourings or aromatisers, buffer substances, and also solvents or solubilisers or agents for achieving a depot effect, as well as salts for changing the osmotic pressure, coating agents or antioxidants. They can also contain two or more compounds of the general formula I or their pharmacologically acceptable acid addition salts and additionally other therapeutically active substances.

Other therapeutically active substances of this type are, for example: β-receptor blockers, such as, for example, propranolol, pindolol, metoprolol; vasodilators, such as, for example, carbocromene; tranquillisers, such as, for example, barbituric acid derivatives, 1,4-benzodiazepines and meprobamate; diuretics, such as, for example, chlorothiazide; cardiotonic agents, such as, for example, digitalis preparations; hypotensive agents, such as, for example, hydralazine, dihydralazine, ramipril, prazosin, clonidine, Rauwolfia alkaloids; agents which lower the fatty acid level in the blood, such as, for example, bezafibrate, fenofibrate; and agents for thrombosis prophylaxis, such as, for example, phenprocoumon.

The compounds of the general formula I, their pharmacologically acceptable acid addition salts, their isomer mixtures and pharmaceutical preparations which contain the compounds of the general formula I or their pharmacologically acceptable acid addition salts or an isomer mixture as active compounds can be used in humans in the control or prevention of disorders of the cardiovascular system, for example as anti-hypertensive medicines in the various forms of high blood pressure, in the control or prevention of angina pectoris, etc. Moreover, they can also be employed for the treatment of erectile dysfunctions. The dose can vary within wide limits and is to be adjusted to the individual conditions in each individual case. In general, in the case of oral administration a daily dose of about 0.5 to 100 mg, preferably 1 to 20 mg, per human individual is adequate. In the case of other administration forms, too, the daily dose, because of the good absorption of the active compounds, is in similar ranges of amounts, i.e. in general also 0.5 to 100 mg/human. The daily dose is normally divided into several, for example 2 to 4, part administrations.

EXAMPLE 1

5,6-Dihydro-4,4-dioxothieno[2,3-c][1,2,5]oxadiazole-1-oxide and -3-oxide a) A solution of 8.4 g (120 mmol) of sodium nitrite in 25 ml of water is added dropwise at 0° C. to a suspension of 15.5 g (116 mmol) of 3-oxotetrahydrothiophene dioxide (M. A. Smith et al., J. Chem. Soc. (c) 1967, 2171) in 70 ml of water and 10 ml of conc. hydrochloric acid. After 1 hour at 0° C., the product is filtered off with suction, washed with water and dried in vacuo.

11.5 g (61%) of 2-hydroxyimino-3-oxotetrahydrothiophene dioxide, m.p. 148° C., are obtained.

b) 5.4 g (77 mmol) of hydroxylamine hydrochloride, dissolved in 15 ml of water, are added to a solution of 11.4 g (70 mmol) of 2-hydroxyimino-3-oxotetrahydrothiophene dioxide in 100 ml of methanol. After 2 hours at room temperature the batch is completely concentrated and the residue is recrystallised from ethanol. 6.2 g (50%) of 2,3-dihydroxyiminotetrahydrothiophene dioxide, m.p. 181° C., are obtained.

c) A solution of 4.4 g (10 mmol) of bis(trifluoroacetoxy)iodobenzene in 280 ml of $CH_2Cl_2$ is added dropwise to a suspension of 1.5 g (8.4 mmol) of 2,3-dihydroxyiminotetrahydrothiophene dioxide in 250 ml of $CH_2Cl_2$ and the mixture is stirred at room temperature for 1 hour. The product partially crystallises out overnight from the completely concentrated batch. After stirring with isopropanol, 1.0 g (68%) of 5,6-dihydro-4,4-dioxothieno[2,3-c][1,2,5]oxadiazole-1-oxide and -3-oxide is obtained in the ratio 1:1 (NMR), m.p. 76° C.

EXAMPLE 2

4H, 6H-4,4,6,6-Tetramethylfuro[3,4-c][1,2,5]oxadiazole-1-oxide a) 10.0 g (54 mmol) of commercially available 2,2,5,5-tetramethyl-3,4-(2H, 5H)-furandione hydrazone oxime are heated under reflux for 2 hours with 75 g (1.1 mmol) of hydroxylamine hydrochloride in 800 ml of water. The precipitated product is filtered off with suction and washed with water. 8 g (86%) of 2,2,5,5-tetramethyl-3,4(2H, 5H)-furandione dioxime are obtained as a mixture of 2 isomers, m.p. 252° C.

b) 90 ml of 14% strength sodium hypochlorite solution are added rapidly at 0° C. to a solution of 3.0 g (16 mmol) of 2,2,5,5-tetramethyl-3,4(2H, 5H)-furandione dioxime in 15 ml of 10% strength sodium hydroxide solution. The deposited precipitate is immediately filtered off with suction, washed with water and recrystallised from isopropanol. 2.0 g (67%) of 4H,6H-4,4,6,6-tetramethylfuro[3,4-c][1,2,5]oxadiazole-1-oxide, m.p. 121° C., are obtained.

EXAMPLE 3

4-Ethyl- and 6-ethyl-5,6-dihydro-4H-cyclopent[c][1,2,5]oxadiazole-1-oxide a) A solution of 5.0 g (40 mmol) of 3-ethyl-2-hydroxy-2-cyclopenten-1-one in 5 g of 1,2-propanediol is added dropwise at 60° C. to a solution of 14 g (200 mmol) of hydroxylamine hydrochloride and 16.5 g (200 mmol) of sodium acetate in 150 ml of water. After 2 hours at 70° C., the deposited precipitate is filtered off with suction and washed with water. 5.0 g (81%) of 3-ethylcyclopentane-1,2-dione dioxime are obtained.

b) 200 ml of 14% strength sodium hypochlorite solution are added dropwise at 0° C. to a solution of 5.0 g (32 mmol) of 3-ethylcyclopentane-1,2-dione dioxime in 200 ml of 10% strength sodium hydroxide solution. After extracting with ethyl acetate and distilling in vacuo at 104° C./0.1 mm Hg, 3.0 g (60%) of 4-ethyl- and 6-ethyl-5,6-dihydro-4H-cyclopent[c][1,2,5]oxadiazole-1-oxide are obtained in the ratio 1:1 (NMR).

EXAMPLE 4

5-Benzoyl-5,6-dihydro-4,4,6,6-tetramethyl-4H-pyrrolo[3,4-c][1,2,5]oxadiazole-1-oxide a) A solution of 0.7 g (2.7 mmol) of 1-benzoyl-2,2,5,5-tetramethylpyrrolidine-3,4-dione (C. Sandris, G. Ourisson, Bull. Soc. Chim. Fr. 1958, 345) and 1.1 g (16 mmol) of hydroxylamine hydrochloride in 60 ml of ethanol/water (1:1) is heated at 60° C. for 10 hours. The deposited precipitate is filtered off with suction, washed with water and dried in vacuo. 0.65 g (83%) of 1-benzoyl-2,2,5,5-tetramethyl-3,4-pyrrolidine dione dioxime, m.p. 235°–240° C. is obtained.

b) 0.55 g (1.9 mmol) of 1-benzoyl-2,2,5,5-tetramethyl-3,4-pyrrolidinedione dioxime is reacted analogously to Example 2b and 0.36 g (66%) of 5-benzoyl-5,6-dihydro-4,4,6,6-tetramethyl-4H-pyrrolo[3,4-c][1,2,5]oxadiazole-1-oxide, m.p. 147°–149° C., is obtained.

EXAMPLE 5

5,6-Dihydro-4,4,6,6-tetramethyl-4H-pyrrolo[3,4-c][1,2,5]oxadiazole-1-oxide 1.3 g (45%) of 5,6-dihydro-4,4,6,6-tetramethyl-4H-pyrrolo[3,4-c][1,2,5]oxadiazole-1-oxide are obtained from 3.1 g (18 mmol) of 2,2,5,5-tetramethylpyrrolidine-3,4-dione-3-oxime analogously to Example 4, $^{13}$C-NMR (DMSO): δ=25.0 (q), 27.5 (q), 66.7 (s), 67.7 (s), 115.6 (s), 164.4 (s), m.p. (hydrochloride): 184°–186° C.

EXAMPLE 6

5,6-Dihydro-5-methyl-4H-pyrrolo[3,4-c][1,2,5]oxadiazole-4-one-1-oxide and -3-oxide a) 10.5 g (0.15 mol) of sodium nitrite in 50 ml of water are added dropwise at 0° C. to a solution of 17.0 g (0.15 mol) of 1-methyl-2,3-pyrrolidinedione (H. Rapoport et al., J. Org. Chem. 40 (1975) 1264). The mixture is stirred for a further 2 hours, the deposited product is filtered off and 12.0 g (58%) of 1-methyl-2,3,4-pyrrolidinetrione-4-oxime are obtained.

b) 9.0 g (63 mmol) of 1-methyl-2,3,4-pyrrolidinetrione-4-oxime are heated at 95° C. for 2 hours with 15 g of hydroxylamine hydrochloride and 15 g of sodium acetate, and 8.5 g (86%) of 1-methyl-2,3,4-pyrrolidinetrione-3,4-dioxime are obtained.

c) A solution of 13.0 g (38 mmol) of potassium hexacyanoferrate(III) in 40 ml of water and 3 ml of saturated sodium carbonate solution is added dropwise to a suspension of 1.0 g (6.4 mmol) of 1-methyl-2,3,4-pyrrolidinetrione-3,4-dioxime in 50 ml of ethyl acetate, and the mixture is stirred at room temperature for 2 hours. The organic phase is separated off and concentrated, and the residue is purified by flash chromatography (ethyl acetate/cyclohexane 60:40). 0.34 g (34%) of 5,6-dihydro-5-methyl-4H-pyrrolo[3,4-c][1,2,5]oxadiazole-4-one-1-oxide and -3-oxide is obtained in the ratio 1:2 (NMR), m.p. 49°–52° C.

EXAMPLE 7

5,6-Dihydro-5-(3,4-dimethoxyphenylethyl)-4H-pyrrolo[3,4-c][1,2,5]oxadiazole-4-one-1-oxide and -3-oxide were obtained analogously to Example 6 (isomers in the ratio 1:4), m.p. 165° C.

EXAMPLE 8

5-Benzyl-6,7-dihydro[1,2,5]oxadiazolo[3,4-c]pyridin-4(5H)-one-1-oxide a) 7 ml of concentrated hydrochloric acid are added at 0° C. to a solution of 7.0 g (34.5 mmol) of 1-benzyl-piperidine-2,4-dione (S. Takano et al., Tetrahedron Lett. 1979, 369) in 30 ml of ethyl acetate and 30 ml of water and then 2.5 g (36 mmol) of sodium nitrite in 10 ml of water are added dropwise. After 1 hour at 0° C., the deposited precipitate is filtered off with suction, and 6.6 g (85%) of 1-benzylpiperidine-2,3,4-trione-3-oxime, m.p. 121°–122° C., are obtained.

b) 3.4 g (68%) of 1-benzylpiperidine-2,3,4-trione-3,4-dioxime, m.p. 170°–172° C., are obtained from 4.6 g of 1-benzylpiperidine-2,3,4-trione-3-oxime analogously to Example 1b.

c) 80 ml of 14% strength sodium hypochlorite solution are rapidly added dropwise at 0° C. to a solution of 3.0 g (12 mmol) of 1-benzylpiperidine-2,3,4-trione-3,4-dioxime in 80 ml of 10% strength sodium hydroxide solution. The deposited precipitate is immediately filtered off with suction, washed with water and dried in vacuo. 2.6 g (87%) of 5-benzyl-6,7-dihydro[1,2,5]oxadiazolo[3,4-c]pyridin-4(5H)-one-1-oxide, m.p. 118°–120° C., are obtained, $^{1}$H-NMR (DMSO): δ=2.95 (t), 3.65 (t), 4.70 (t), 7.35 (s), $^{13}$C-NMR (DMSO): δ=18.0 (t), 44.8 (t), 49.2 (t), 111.9 (s), 127.4 (d), 127.7 (d), 128.5 (d), 136.2 (s), 149.6 (s), 155.7 (s).

EXAMPLE 9

5-Benzyl-6,7-dihydro[1,2,5]oxadiazolo[3,4-c]-pyridin-4(5H)-one-3-oxide 1.6 g of 5-benzyl-6,7-dihydro[1,2,5]oxadiazolo[3,4-c]-pyridin-4(5H)-one-1-oxide are heated under reflux for 4 hours in 200 ml of toluene. The toluene is stripped off and the residue is recrystallised from isopropanol. 1.4 g of 5-benzyl-6,7-dihydro[1,2,5]oxadiazolo[3,4-c]-pyridin-4(5H)-one-3-oxide and -1-oxide are obtained in the ratio 4:1, m.p. 112°–114° C., $^{1}$H-NMR (DMSO): δ=3.10 (t), 3.65 (t), 4.65 (s), 7.35 (s).

EXAMPLE 10

Thieno[2,3-c][1,2,5]oxadiazole-5-carboxamide-1-oxide and -3-oxide

A suspension of 25.0 g (90 mmol) of ethyl 2-bromo-3-nitro-5-thiophenecarboxylate (Tetrahedron 21 (1965) 1061) and 29.0 g (450 mmol) of sodium azide in 300 ml of methanol is stirred at room temperature for 4 hours in 300 ml of ethanol. The mixture is poured into 4 l of ice-water, the precipitate is filtered off and the residue is heated at 70° C. for 3 hours in 700 ml of toluene. Subsequent purification by flash chromatography yields 6.5 g (34%) of ethyl thieno[2,3-c][1,2,5]oxadiazole-5-carboxylate-1-oxide and -3-oxide, m.p. 72°–74° C.

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We claim:

1. Fused 1,2,5Oxadiazole-2-oxide of the formula

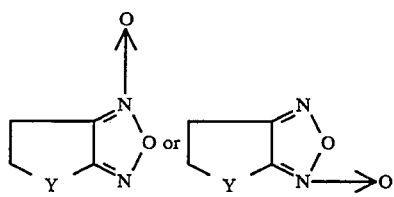

in which Y denotes —S—, —S(O)—, or —S(O)$_2$—.

2. Isomer mixture of fused 1,2,5-oxadiazole-2-oxides according to claim 1.

3. Process for the treatment of angina pectoris, which comprises administering effective amounts of a 1,2,5-oxadiazole-2-oxide according to claim 1 to a patient in need thereof.

4. Process for the treatment of angina pectoris, which comprises administering effective amounts of an isomer mixture of 1,2,5-oxadiazole-2-oxides according to claim 2 to a patient in need thereof.

5. Pharmaceutical composition for the treatment of angina pectoris containing a fused 1,2,5-oxadiazole-2-oxide as claimed in claim 1 or an isomer mixture thereof as active compound.

6. Pharmaceutical composition for the treatment of angina pectoris containing an isomer mixture of fused 1,2,5-oxadiazole-2-oxides as claimed in claim 2 as active compound.

* * * * *